United States Patent [19]

Tolman

[11] Patent Number: 4,732,864

[45] Date of Patent: Mar. 22, 1988

[54] TRACE-LABELED CONJUGATES OF METALLOTHIONEIN AND TARGET-SEEKING BIOLOGICALLY ACTIVE MOLECULES

[75] Inventor: Glen L. Tolman, Chelmsford, Mass.

[73] Assignee: E. I. Du Pont de Nemours and Company, Wilmington, Del.

[21] Appl. No.: 539,733

[22] Filed: Oct. 6, 1983

[51] Int. Cl.$^4$ .................... G01N 33/53; A61K 43/00; C07K 7/00

[52] U.S. Cl. ............................ 436/547; 436/548; 436/804; 436/173; 424/1.1; 424/9; 424/85; 128/653; 128/654; 530/400; 530/402

[58] Field of Search ............ 260/113; 424/4, 9, 85, 424/1.1; 436/547, 548, 804; 530/400, 402; 128/653, 654

[56] References Cited

U.S. PATENT DOCUMENTS 4,472,509  9/1984  Gansow et al. ............... 436/548

FOREIGN PATENT DOCUMENTS 0035765  9/1981  European Pat. Off. .
0083129  7/1983  European Pat. Off. .
2109407A  6/1983  United Kingdom .

OTHER PUBLICATIONS

Hosain, et al., J. Nucl. Med., vol. 14, No. 6, (1973), p. 410.
Krantz, et al., Biochemistry, vol. 15, No. 18, (1976), pp. 3963–3968.
Pritchard, et al., Proc. Soc. Exp. Biol. Med., 151:297–302, (1976).
Ban An Khaw, et al., Science, 209: 295–297, (1980).
D. Colcher, et al., Proc. Natl. Acad. Sci., U.S.A., 78: 3199–3203, (1981).
Robert C. Brasch, M.D., Radiology, 147: 781–788, (1983).
Metallothioneins, pp. 46–92, Jul. 17–22, 1978, Kagi and Noldberg.
Rupp and Weser, Biochimica et Biophysica Acta, 533, p. 209, (1978), Disclosing Zn, Cd, and Hg Metallothionein.
Yoshida et al., Proc. Natl. Acad. Sci., U.S.A., 76, p. 486, (1970), Disclosing Zn, Cd, and Hg Metallothionein.
Webb and Cain, Biochemical Pharmacology, 31, p. 137, (1982), Disclosing Cd, Zn and Cu Metallothionein.
Nordberg and Nordberg, Environmental Health Perspectives, 12, p. 103, (1975).
Vander Mallie and Garvey, Immunochemistry, 15, p. 857, (1978).
Kagi and Vallee, J. Biol. Chem., 236, p. 2435, (1961), Disclosing CD and Zn Metallothionein.

Primary Examiner—Robert J. Warden
Assistant Examiner—Stephen C. Wieder

[57] ABSTRACT

Conjugates of target-seeking biologically active molecules and metallothionein in which all or part of the metal in the metallothionein is suitable for diagnostic or therapeutic applications.

44 Claims, No Drawings

TRACE-LABELED CONJUGATES OF METALLOTHIONEIN AND TARGET-SEEKING BIOLOGICALLY ACTIVE MOLECULES

FIELD OF THE INVENTION

This invention relates to target-seeking biologically active molecules which are trace-labeled by covalent conjugation to a bifunctional metal chelate in which at least a part of the metal in the chelate is suitable for diagnostic or therapeutic applications. Such target-seeking biologically active molecules include antibodies or antibody fragments or any other compound which localizes selectivity in certain organs, tissues or cells of a mammalian body.

BACKGROUND

Use of radiolabeled target-seeking biologically active molecules (hereinafter referred to as BAMs), especially antibodies and other proteins, for diagnostic and therapeutic purposes is a highly active field. For a discussion of such radiolabeling, see Eckelman et al., Radiolabeling of Antibodies, *Cancer Research*, 40: 3036–3042 (1980) and Sfakianakis et al., Radioimmunodiagnosis and Radioimmunotherapy, *J. Nucl. Med.* 23: 840–850 (1982). The most widely used means of radiolabeling antibodies has been direct iodination with I-131, I-125 or I-123. However, these radionuclides have certain dosimetric and imaging disadvantages. Certain metallic radionuclides such as Tc-99m and In-111 are more suitable for scintigraphic imaging. However, it has heretofore been difficult to attach these metallic radionuclides directly to most BAMs because generally there is insufficient affinity between the radionuclide and the BAM. Further, in some cases where such attachment has been possible, the attachment of radionuclide sometimes results in partial or complete loss of the biological activity of the BAM.

For these reasons, it has been proposed by many in the art to radiolabel BAMs with metallic radionuclides by covalent conjugation using a metal chelating agent. For example, Khaw et al., *Science* 209: 295–297 (1980) discloses antibodies to cardiac myosin labeled with In-111 diethylenetriaminepentaacetic acid (DTPA) and use of the labeled antibodies to image for myocardial infarction. Krejcarek et al., *Biochem. Biophys. Res. Commun.* 77: 581–585 (1977) discloses use of DTPA to label proteins such as human serum album (HSA) with metal radionuclides. Pritchard et al., *Proc. Soc. Exp. Biol. Med.* 151: 297–302 (1976) discloses conjugation of antibodies to various agents capable of chelating In-111, such as transferrin, D-penicillamine and deferoxamine. Yokoyama et al., European Patent Application No. 35,765, published in 1981, discloses deferoxamine as a bifunctional chelator for radiolabeling various BAMs, including proteins (e.g., HSA, urokinase, fibrinogen), antibiotics (e.g., "Bleomycin", "Kanamycin") hormones, saccharides and fatty acids. Haber et al., European Patent Application No. 38,546 published in 1981, discloses DTPA, ethylenediaminetetraactic acid (EDTA) and ethylenediamine as bifunctional chelators for radiolabeling proteins, including antibodies, antigens and antibody fragments. Yokoyama et al., U.S. Pat. No. 4,287,362 issued in 1981 discloses 3-carboxy-2-oxopropionaldehyde bis(N-methylthiosemicarbazone) (OPBMT) and analogs as bifunctional chelating agents for radiolabeling proteins. Sundberg et al., U.S. Pat. No. 3,994,966, issued in 1976, Meares et al., U.S. Pat. No. 4,043,998 and Leung et al., *Int. J. App. Radiation and Isotopes* 29: 697–692 (1978) disclose bifunctional EDTA analogs such as 1-(p-benzenediazonium)-EDTA and 1-p-aminophenyl-EDTA for protein labeling. Paik et al., *J. Radioanal. Chem.* 57: 553–564 (1980) discloses an azo derivative of DTPA called DTTA-azo-imidate as a bifunctional chelator and its use to label HSA with In-111. Each of the bifunctional chelators heretofore described, however, has generally been designed to coordinate a specific metallic radionuclide. It would, therefore, be desirable to develop a chelator capable of coordinating a variety of metallic cations, and capable of conjugation with BAMs, while retaining the biological activity of the BAMs.

Further, current intravascular radiographic contrast agents are based upon iodinated aromatic compounds. These compounds, however, are often found not to be physiologically tolerable at useful concentrations. Therefore, it would be desirable to develop physiologically compatible alternatives to such iodinated compounds.

Also, in the rapidly developing field of nuclear magnetic resonance (NMR) imaging, useful contrast agents would be valuable, particularly if capable of conjugation with BAMs. Brasch (*Radiology*, 147: 781–788, (1983)) in his review of methods of contrast enhancement for NMR imaging, notes among criteria for the "ideal" contrast enhancer, that the compound should have strong NMR activity at low concentrations, be non-reactive in vivo, and should be non-toxic in diagnostic doses.

SUMMARY OF THE INVENTION

The subject invention relates to the use of metallothionein as a carrier of trace-label metal in the labeling of BAMs. In addition to the wide variety of metals metallothionein will coordinate, it also offers the advantage of binding as many as ten gram atoms of metal per molecule. Therefore, metallothionein will bind a wide variety of trace-label metals and offers the option of incorporating from one to ten moles of metal per mole of bifunctional chelator. Surprisingly, conjugation of metallothionein to BAMs does not compromise the biological activity of the BAMs.

This invention provides conjugates of BAMs and metallothionein or metallothionein fragments in which at least a portion of the metal in the metallothionein or fragment is a radionuclide, or non-radioactive, trace-label metal, having sufficient affinity for the metallothionein or fragment to bind thereto. Preferably, such trace label metal is selected from In, Pb, Tc, Ru, Hg, Ag, Au, Pd, Cu, Re, Sb, Bi, Ga, Pt, W, Co, Ni, Rh and Os.

Further, the subject invention includes covalent conjugates of BAMs and metallothionein or metallothionein fragments in which all metal in the metallothionein or fragment is a non-trace-label metal, such as Zn. These conjugates are useful as intermediates for preparing the trace-labeled conjugates of this invention through exchange labeling, i.e., by replacement of at least a portion of the non-trace-label metal with a metallic trace-label.

This invention also includes trace-labeled conjugated metallothionein or metallothionein fragments in which all or part of the metal is a metallic trace-label. These trace-labeled, unconjugated metallothioneins can be used, inter alia, as intermediates to produce the trace-labeled, conjugated metallothionein of this invention.

DETAILED DESCRIPTION

Metallothioneins

Metallothioneins are described in *Metallothioneins: Proceedings of the First International Meeting on Metallothionein and Other Low Molecular Weight Metal-Binding Proteins,* Zurich, July 17-22, 1978, ed. by Kagi and Nordberg, Birkhauser Verlag Basel, 1979 (hereinafter Kagi and Nordberg). Pages 46-92 of Kagi and Nordberg are incorporated herein by reference and summarized below. Metallothionein was discovered in 1957; the cadmium and zinc containing protein was isolated from equine kidney. Substantially the same protein was later found in rabbits, humans, monkeys, cattle, sheep, pigs, dogs, hamsters, rats, mice and seals. Equine metallothionein was characterized as having: molecular weight of 6000-7000; high metal content; high cysteine content; no aromatic amino acid; optical features of metal thiolates (mercaptides) and fixed distribution of cysteinyl residues. It was agreed by the plenum of the First International Meeting on Metallothioneins, referred to above, that proteins resembling equine renal metallothionein in several of these features can be designated as "metallothionein" (Kagi and Nordberg, p. 48), and this is the manner in which the term is used in this specification. Of course, metallothionein fragments are also useful in the practice of the subject invention as are functionally similar polypeptides having at least about six amino acid residues.

Generally speaking, metallothioneins are low molecular weight proteins which are produced in vivo and which chelate a wide variety of metal ions with high affinity. The physiological function of metallothioneins is not well-understood, but it is generally accepted that they function in the homeostasis of essential metals and the detoxification of heavy metals. Metallothioneins are ubiquitous to higher vertebrates, invertebrates, and eukaryotic and prokaryotic microorganisms. Exposure of many organisms to metal ions of e.g., Cd, Hg, Zn or Cu induces rapid de novo synthesis of metallothioneins by enhanced production of the mRNA for apoprotein thionein. Therefore, molecules such as cadystin, produced by certain microorganisms in response to Cd injection, are also contemplated for use in the subject invention.

All mammalian thioneins contain 60-61 amino acid residues and can bind 7 gram-atoms of divalent or up to 10 gram-atoms of monovalent metal ion per mole. Thioneins contain no aromatic or histidine residues, and 20 of the amino acid residues in mammalian thioneins are cysteines. Based on spectroscopic evidence, metal ligation by thionein is almost exclusively through the sulfhydryl moieties of the cysteines.

Because the sulfhydryl moieties in metallothioneins are bound to metal ions, they are generally not available to serve as functional groups for conjugation to BAMs, but other groups such as $-NH_2$, $-OH$ and $-COOH$ groups are available, and the metallothioneins can thus be covalently conjugated to BAMs using reagents and methods which utilize these groups as detailed below.

Complete amino acid sequences for several metallothioneins have been determined; they are reported on page 60 of Kagi and Nordberg and selected ones are repeated here:

TABLE 1

Amino Acid Sequences of Metallothioneins (MT)

| 1 | 10 | 20 | 30 | 40 | 50 | 60 |

Human MT-2
Ac-MDPNCSCAAGDSCTCAGSCKCKECKCTSCKKSCCSCCPVGCAKCAQGCICKGASDKCCSCA-OH
Equine MT-1A
Ac-MDPNCSCPTGGSCTCAGSCKCKECRCTSCKKSCCSCCPGGCARCAQGCVCKGASDKCCSCA-OH
Mouse MT-I
Ac-MDPNCSCSTGGSCTCTSSCACKDCKCTSCKKSCCSCCPVGCSKCAQGCVCKGAADKCTCCA-OH
Neurospora MT
H-GDCGCSGASSCNCGSGCSCSNCGSK-OH One-letter symbols:
A = Alanine
C = Cysteine
D = Aspartic acid
E = Glutamic acid
G = Glycine
I = Isoleucine
K = Lysine
L = Leucine
M = Methionine
N = Asparagine
P = Proline
Q = Glutamine
R = Arginine
S = Serine
T = Threonine
V = Valine
Other symbols:
Ac = Acetyl
H = Free amino terminus
OH = Free carboxyl terminus It will be observed that the cysteine residues are distributed along the chain and that there are a number of -C-X-C- residues, where X stands for an amino acid other than cysteine. The table includes a metallothionein from *Neurospora crassa* with a much lower molecular weight than the mammalian metallothioneins. As reported on p. 55 of Kagi and Nordberg, higher molecular weight metallothioneins (9500-10,000) have been isolated from other microorganisms. All of these metallothioneins are within the scope of the invention, although the mammalian metallothioneins are preferred. For in vivo diagnostic and therapeutic purposes, it is especially preferred to use a metallothionein from the same species as the mammal being treated.

Metal-binding fragments of thionein, for example, as reported in Yoshida et al., *Proc. Natl. Acad. Sci., U.S.A.* 76: 486-490, and in Kondo et al., *Tetrahedron Letters,*

24: 925-928, both hereby incorporated by reference, can also be used in this invention. The fragments of mouse thionein synthesized by Yoshida et al. have the following amino acid sequences in which the letter symbols have the same meaning as in Table 1 above.

1. H₂N-K-C-T-C-C-A-OH
2. H₂N-A-C-K-D-C-K-C-T-OH
3. H₂N-S-C-T-C-T-S-S-C-A-OH
4. H₂N-G-C-S-K-C-A-Q-G-C-V-OH
5. H₂N-G-C-V-K-G-A-A-D-K-C-T-C-A-OH

Metal-bound fragments of thioneins (i.e., metallothionein fragments) such as those synthesized by Yoshida et al. are suitable for use in this invention, although complete metallothioneins are presently preferred.

Of course, it will be apparent to those skilled in the art that polypeptides having functional similarities to metallothionein, as well as copolymers of metallothionein/metallothionein fragments and conventional monomers, made using conventional synthetic techniques, are useful in the practice of the subject invention so long as they exhibit the general characteristics of metallothionein as detailed above.

Metallic Trace-Labels

Of the diagnostic and therapeutic radionuclides heretofore known, the following are among those useful in the practice of the subject invention (half-life given in d=days, h=hours):

TABLE II

| Diagnostic Radionuclide | Half life |
|---|---|
| Ruthenium-97 | 2.9 d |
| Technetium-99 m | 6.0 h |
| Mercury-197 | 2.7 d |
| Gallium-67 | 77.9 h |
| Gallium-68 | 1.1 h |
| Osmium-191 | 15 d |
| Indium-111 | 2.8 d |
| Indium-113 m | 1.7 h |
| Lead-203 | 52 h |

| Therapeutic Radionuclide | Half Life |
|---|---|
| Palladium-103 | 17.0 d |
| Silver-111 | 7.5 d |
| Antimony-119 | 1.6 d |
| Gold-198 | 2.7 d |
| Copper-67 | 2.6 d |
| Rhenium-188 | 17.0 h |
| Bismuth-212 | 1.0 h |

The diagnostic radionuclides are gamma-emitters and/or positron-emitters, emitting energies between 30 KeV and 1 MeV and possessing half-lives of between about 1 minute and 8 days. These radionuclides are useful in conjunction with conventional radioscintigraphic imaging techniques based upon, e.g.. planar, single photon or positron tomographic methods. The therapeutic radionuclides emit alpha-, beta-, gamma, conversion electrons or Auger electrons of energies between 100 eV and 2 MeV, and are capable of killing cells in vivo.

Of course, those skilled in the art will appreciate that when discussing diagnostic and therapeutic uses for these various radionuclides, the dosages utilized will depend upon many variables. When utilizing the radionuclides for imaging purposes, the particular dosage employed need only be high enough to obtain diagnostically useful images, generally in the range of 0.1 to 20 mCi/70 Kg body weight. In contrast, the therapeutic purposes, higher doses can be utilized, generally in the range of 0.1-500 mCi/70 Kg body weight. Of course, the proper dose will ultimately depend on the physical properties of radionuclide such as half-life, type of radiation, and energy of radiation, and on the pharmacokinetics of the radiolabeled agent.

Of the contrast agents heretofore known as being useful for NMR imaging, cobalt, nickel, copper and ruthenium are considered useful in the practice of the subject invention.

Of the contrast agents heretofore known as being useful for radiographic imaging, metallic elements in the periodic table numbered 72 to 83 are considered useful in the practice of the subject invention, and bismuth, lead, mercury, gold, platinum, rhenium and tungsten are preferred.

Trace-Labeling Metallothionein

There are generally two procedures which can be utilized to produce trace-labeled metallothionein. The first is by direct labeling of thionein. The second is by exchange labeling a metallothionein such as Zn-metallothionein using a desirable metal trace-label.

The first procedure, i.e., the direct labeling of thionein with trace-label, is similar to that reported by M. Vasak and J. Kagi, Proc. Natl. Acad. Sci. USA, 78: 6709 (1981) hereby incorporated by reference. Generally, mammalian thionein is dissolved at pH 2 and any resulting insoluble material removed by filtration. To this solution of thionein, the metal trace-label and any desired non-trace-label metal cation are added. The total concentration of trace-label and non-trace-label metal cation should be sufficient to insure that there are available at least seven divalent or ten monovalent metal cations per thionein, or suitable combinations of divalent and monovalent cations to fill all metal binding sites on the metallothionein. Because of the unique properties of thionein, metallothioneins containing more than one metal cation can be prepared. Therefore, since it is possible that all the metal-binding sites of thionein can be occupied by metal trace-label, trace-labeled metallothioneins of very high concentrations can be prepared.

When utilizing a radionuclide as the metal trace-label, the concentration of radionuclide added depends on the specific activity required for the clinical application of interest. For diagnostic applications, the ratio of moles of radionuclide per mole of thionein may be as small as one or less. For therapeutic applications, this ratio may be higher. Non-radioactive metal cations may be added in quantities sufficient to occupy the metal binding sites not occupied by radioactive cations. Following the addition of radionuclides, and optionally non-radioactive metal cation, the resulting solution is extensively degassed to remove oxygen and neutralized in an inert atmosphere until the pH is greater than 7.0. During this neutralization the thionein folds around the radionuclide and non-radioactive metal cations to form the desired radiolabeled metallothionein. The labeled metallothionein can then be purified by conventional techniques such as dialysis, size exclusion or ion echange chromatography. The non-radioactive metal content of the radiolabeled metallothionein can be determined by atomic absorption and the radionuclide content assessed by couting radioactive decay. This purified radionuclide-labeled metallothionein can then be coupled directly to a BAM using bifunctional coupling or crosslinking agents described below. Because of the time required to prepare radionuclide-labeled metallothionein and couple them to desired BAMs, radionuclides such as Ru-97 and Hg-197 with half-lives of greater than 24 hours are preferred for use in this direct labeling technique.

The second labeling procedure involves the exchange of a trace-label metal cation for all or a portion of the non-trace-label metal cations of metallothionein. The success of this exchange reaction requires that the trace-label cation have a higher affinity for the mercaptides of metallothionein than the non-trace-label cation in the preformed metallothionein.

For example, when utilizing radionuclides as the metal trace-label, zinc cations have a lower affinity for the mercaptides of metallothionein than cations of either technetium, mercury, or silver. Therefore, in the presence of cations of technetium-99m, mercury-197, or silver-111, the Zn (II) cations of Zn-metallothionein (MTh) are readily displaced to give Zn/$^{99m}$Tc-MTh, Zn/$^{197}$Hg-MTh, or Zn/$^{111}$Ag-MTh, respectively. Thus, since Zn-MTh is easily prepared by the procedure of Vasak et al., supra, exchange labeling of Zn-MTh or a conjugate of Zn-MTh—BAM can be accomplished by mixing Zn-MTh or Zn-MTh—BAM conjugate with a soluble, exchangeable species of radionuclide, e.g., $^{99m}$Tc-glucoheptonate, $^{197}$HgCl$_2$, or $^{111}$Ag(NH$_3$)$^+$$_2$. Following exchange, the radiolabeled metallothionein can be purified by conventional techniques such as dialysis, size exclusion or ion exchange chromatography. The yield of exchange labeling can be determined by counting the radioactive decay and represents the percentage of total radioactivity which is incorporated into the metallothionein. Cobalt (II), nickel (II), and zinc (II) cations from metallothioneins that can be utilized in an exchange labeling process involving the radionuclides listed in Table 2; however, zinc (II) cations are the preferred non-radioactive cations for this exchange labeling. The use of the exchange labeling procedure is useful especially when utilizing radionuclides with half-lives shorter than 24 hours because this exchange labeling can be carried out at the clinical site. As further discussed below, exchange labeling of a Zn-MTh—BAM conjugate with short-lived radionuclides makes possible the introduction of radionuclides immediately before use and avoids the inevitable loss of radioactivity through decay.

Of the radionuclides mentioned above, $^{99m}$Tc is most preferred in the practice of the subject invention for exchange labeling due to its relatively short half-life, because of its ready availability from Mo-99/Tc-99m generators, and because of the desired physical characteristics of the radionuclide. The radionuclides Ag-111, Au-198 and Hg-197 are most preferred for either direct labeling of thionein or exchange labeling due to the ease in which both labeling procedures can be carried out. The radionuclides Ru-97, Pd-103 and Sb-119 are best utilized through direct thionein labeling procedures.

As mentioned above, these radiolabeled metallothioneins can be used as intermediates to produce radiolabeled metallothionein—BAM conjugates of the invention as detailed below. Also, $^{99m}$Tc-labelled metallothioneins or metallothionein fragments may be particularly useful per se as kidney function imaging agents. The organ distribution of radiolabled metallothioneins have been reported utilizing the radionuclides Zn-65 and Cd-109 but neither of these radionuclides have physical properties or dosimetry appropriate for in vivo diagnostic imaging. The $^{99m}$Tc/Zn-MTh prepared by the exchange labeling procedure outlined above may be used in vivo for diagnosing disorders of the kidney. Following intravenous injection of $^{99m}$Tc/Zn-MTh, in mice, the $^{99m}$Tc/Zn-MTh is cleared immediately by the kidney. At fifteen minutes post injection, 75% of the $^{99m}$Tc activity resides in the kidney, bladder, and urine. Thus, the function of the kidney can be assessed very rapidly in vivo by following the clearance of $^{99m}$Tc/Zn-MTh. The inherent advantage of using $^{99m}$Tc/Zn-MTh over other diagnostic kidney agents such as $^{99m}$TcDTPA is that metallothionein is an integral part of the detoxification mechanism developed by nature. In humans, the kidney plays a key role in the metabolism of heavy metal metallothioneins.

Methods analogous to those described for radiolabeling metallothionein may be used for incorporation of non-radioactive metallic trace-labels. Of those which would be useful for radiographic contrast, i.e., Bi, Rh, Hg, Au, Pt, Re and W, mercury and gold can be incorporated into metallothionein by exchange labeling or by direct conjugation to the apoprotein. Incorporation of the remaining elements is achieved by direct labeling. Of those which would be useful for NMR imaging, i.e., Co, Ni, Cu(II) and Ru, copper (II) is best incorporated into metallothionein by exchange labeling, whereas cobalt, nickel and ruthenium are incorporated by direct labeling.

Target-Seeking Biologically Active Molecules

The term target-seeking biologically active molecules (BAM) as used herein means antibodies (especially monoclonal antibodies), Fab, Fab' and F(ab')$_2$ fragment of antibodies, and other molecules which localized in certain organs, tissues or cells of the mammalian body. Examples of such other molecules are hormones such as insulin, glucagon, prostaglandins, steroidal hormones, and peptides, and other proteins which bind specifically to certain cell types, such as luteinzing hormone which binds to receptors in ovaries. Large molecules such as proteins are generally preferred for radiolabeling through metallothionein conjugation, but conjugation of several small molecules may also be suitable; for example, conjugation to radiolabeled metallothionein of several molecules of quinuclidinyl benzilate, which binds to muscarinic cholinergic receptors of the heart, would provide a radiopharmaceutical for following the viability of the heart cells in vivo. Estrogen and neuropeptides conjugated to radiolabeled metallothioneins could likewise provide breast tumor and brain perfusion agents, respectively.

Surprisingly, it has been discovered that BAMs, for example monoclonal antibodies Anti-THY 1.1 (L. L. Houston, R. C. Nowinski, and I. D. Bernstein, *J. Immunology*, 125: 837 (1980) hereby incorporated by reference), and anti-human breast carcinoma B6.2 (D. Colcher, et al., *Proc. Natl. Acad. Sci. USA*, 78: 3199 (1981)) as well as other can be conjugated to Zn-metallothionein and the conjugate exchange labeled with, e.g. Tc-99m, without substantially decreasing the immunoreactivity of the BAMs.

Conjugation

BAMs can be conjugated to metallothioneins either before or after radiolabeling of the metallothionein. It is generally preferred to radiolabel before conjugation, because harsher conditions can be used for radiolabeling than for conjugation. However, when it is desired to radiolabel by exchange labeling with a short-lived radionuclide, such as Tc-99m, just prior to clinical use, conjugation before radiolabeling, as exemplified below, is preferred.

Mammalian metallothioneins typically include the following amino acid residues which possess functional groups through which metallothioneins can be directly conjugated to BAMs: cysteine, 20 thiol (—SH) groups; lysine, 8 amino (—NH$_2$)groups; aspartic/glutamic acid, 4 or 5 carboxyl (—COOH) groups; and serine/threonine, 10 to 14 hydroxyl (—OH) groups. Not every amino acid residue in metallothionein is available for conjugation because some participate in various functions within the metallothionein. The cysteine SH groups are involved in metal binding and generally do not react with reagents targeted for thiols under normal conditions. The use of partially metallated metallothionein or fragments of matallothionein permits reaction of —SH groups not utilized for metal binding. Removal of part of the metal from the metallothionein to make such —SH groups available for direct conjugation can be done by treatment with strong chelating agents such as EDTA or DTPA. The lysine and arginine residues are largely unavailable for conjugation because they participate in electrostatic bonds with the highly negative metal clusters in metallothioneins. Although some (1 to 3) of the lysines are normally available, exposure of metallothionein to solutions of high ionic strength leads to breakdown of electrostatic bonds and results in greater availability of lysine and arginine residues. The carboxyl and hydroxyl groups on the surface of metallothionein are generally available for conjugating to BAMs, and may therefore be most preferable for conjugation.

The attachment of BAMs to radiolabeled metallothioneins generated by direct labeling of thionein or non-radioactive metallothioneins for subsequent exchange labeling with radionuclide requires conjugating the available —SH, NH$_2$, —NHC(=NH)NH$_2$, —CO$_2$H, or OH groups of metallothioneins to complementary functional groups on the BAM. If the BAM is a monoclonal antibody or other glycoprotein, it will contain the same functional groups as metallothionein, i.e., —SH—NH$_2$, —OH, —CO$_2$H, and NHC(=NH)NH$_2$. When dealing with smaller drugs or hormones that do not contain such groups, one of these groups may be synthetically incorporated into the small molecule so that conjugation with metallothionein can take place. Methodology will vary widely from one such drug or hormone to another, as is well known to those skilled in the art, a prime consideration being the preservation of biological specificity and affinity. For a general discussion of such synthetic modification, see Means and Feeney, "Chemical Modification of Proteins," Holden-Day, Inc. (1971) hereby incorporated by reference. Thereafter, the metallothionein and the BAM can be conjugated directly utilizing appropriate reagents and methods. In general, for the conjugating of proteins to metallothionein, as well as for modification of metallothioneins or proteins for conjugation, mild conditions are required to avoid denaturation of the metallothionein and BAM and loss of biological activity. The pH of the reaction should be in the range of about 3 to 11, preferably 5 to 9, temperature in the range of 0° to 60° C., and concentrations of each BAM and metallothionein in the range of $10^{-2}$ to $10^{-6}$M, preferably about $10^{-4}$M. The preferred solvent is generally water although varying amounts of solvents like dimethyl sulfoxide can be added to dissolve non-polar conjugating agents. For conjugating non-proteinaceous BAMs to metallothioneins, somewhat harsher conditions can be tolerated by the metallothionein and reactions can be run in organic solvents like dimethyl sulfoxide.

If the metallothionein and BAM do not contain complementary conjugating moieties, in lieu of synthetically modifying either or both metallothionein or BAM, it is possible to employ crosslinking agents to effect the desired conjugation. The crosslinking agent should contain two chemically compatible receive groups X and Y that form covalent bonds with functional groups on metallothionein and the BAM and that are connected by an alkyl and/or aryl chain, i.e., X-C$_n$-Y where C$_n$ is alkyl or aryl. The reactive groups X and Y must be chemically compatible, i.e., they must not react with each other to produce polymeric species. Since metallothionein and most BAMs contain —NH$_2$, —SH and —OH groups, among the preferred reactive groups for X and Y are alkylating and acylating groups. The preferred alkylating groups for X and Y are $\alpha$-haloacids, $\alpha$-haloesters, or $\alpha$-haloamides; aryl halides; nad maleimides. Crosslinking through the use of reductive alkylation of —NH$_2$ groups on the metallothionein and BAM is also preferred; crosslinking agents like glutaraldehyde where X and Y are aldehydes and n=3 have demonstrated utility in attaching radiolabeled metallothioneins to monoclonal antibodies through reductive alkylation of such —NH$_2$ groups. Preferred acylating agents for X and Y include activated carboxyl functionalities such as chlorides and anhydrides, imidoesters, thioesters, and N-hydroxysuccinimide esters. In general, the acylation of amines is preferred over hydroxyls since amides are known to be more stable in vivo then esters.

The preferred moieties for X and Y in forming covalent bonds with —NHC(=NH)NH$_2$ groups include 1,2- and 1,3-dicarbonyl compounds like malondialdehyde, cyclohexane-1,2-dione, and camphorquinone. The reaction of arginine residues with these reagents is very selective and is reversible.

The preferred moiety for X and Y in utilizing carboxy groups of metallothionein and BAM for crosslinking is the amine group. When activated by a water-soluble carbodiimide such as 1-cyclohexyl-3-(2-morpholinyl-4-ethyl)carbodiimide or 1-ethyl-3-(3-dimethyl-aminopropyl)carbodiimide, the activated carboxyl group of metallothionein or BAM will react with X and/or Y=—NH$_2$ of a crosslinking agent to form a amide bond. Reaction of such carboxyl groups on metallothionein and BAMs with crosslinking agents containing amino groups is a preferred method of attaching metallothionein to BAMs.

In general, the carbon chain separating X and Y can be either alkyl or aryl with n=1 to 12. The choice of chain length varies depending on the nature of the BAM being attached. With large BAMs, a longer chain may be required to allow optimal covalent bond formation between the crosslinking agent bound to metallothionein and the target functional groups on the large protein. With small BAMs, a very long carbon chain may be required to allow for the BAM attached to metallothionein to interact with its cell surface receptor. The chain length can thus be varied either to optimize the crosslinking process or to maximize the retention of biological activity of the metallothionein-BAM conjugate.

Some commercially available crosslinking agents are preferred in attaching metallothioneins to monoclonal antibodies. Examples of preferred crosslinking agents include glutaraldehyde, N-(2-chloroethyl)maleimide, disuccinimidyl tartarate, succinimidyl 4-p-maleimidophenyl)butyrate, 2-iminothiolane, and dimethyl adipimidate.

The trace-labeled conjugates of this invention are used in the same manner as prior art trace-labeled BAMs. They can be lyophilized for storage and shipment then reconstituted in a physiologically acceptable vehicle, e.g. normal physiological saline and injected intravenously for diagnostic imaging or therapy, or they can be prepared immediately before use by exchange labeling. They can also be used in in vitro assay and clinical diagnostic methods in the same manner as prior art trace-labeled compounds.

EXAMPLE 1

Preparation of Mercury-203 Labeled Metallothionein from Thionein

Thionein was obtained from rabbit liver by the method of M. Vasak, et al, *Biochemistry*, 20: 2852 (1981). This thionein (3–5 mg) was dissolved in 1.0 ml of metal-free 0.1N HCl and filtered to remove any undissolved material. The concentration of the resulting thionein was determined spectrophotometrically utilizing an absorption coefficient at 220 nm of 7.9 $mg^{-1}$ $ml/cm^{-1}$ for calculation. To a solution of this thionein (0.5 mg/ml) was added 0.76 mCi of $^{203}HgCl_2$ (specific activity = $8.76 \times 10^2$ mCi/mmol). The resulting thionein/$^{203}HgCl_2$ solution was degassed thoroughly to remove oxygen by alternately freezing and thawing the mixture in vacuo. Under an atmosphere of argon, the thionein/$^{203}HgCl_2$ was neutralized with metal-free 0.5M tris(hydroxymethyl)aminomethane (Tris) buffer to a pH greater than 7.0. The resulting $^{203}$Hg-MT was evaluated by size exclusion HPLC using an I-60 gel filtration column (available from Waters Assoc., Inc., Milford, Mass.) eluting with 0.025M phosphate buffer (pH 7.0) at 2.0 ml/min. After chromatography, 98% of the $^{203}$Hg radioactivity added remained with the $^{203}$Hg-MT. Because there is no isotope effect with regard to metallothionein preparation, the substitution of $^{197}HgCl_2$ will give comparable results.

EXAMPLE II

Preparation of Zn/$^{99m}$Tc-Metallothionein by Exchange Labeling of Zn-Metallothionein Zn-Metallothionein was prepared by the method of M. Vasak and J. Kagi, *Proc. Natl. Acad. Sci. USA*, 78: 6709 (1981) using non-radioactive $ZnSO_4.7H_2O$ and dialyzed using "Spectra Por 6" dialysis tubing (2000 MW cutoff) available from Spectrum Medical Instruments, Inc., Los Angeles, Calif., against 0.01M phosphate buffer (pH 6.5). To 0.5 mg of Zn-metallothionein (1.0 ml; $10^{-4}$M) was added 9.7 mCi of $^{99m}$Tc-GLUCOSCAN ™ (New England Nuclear Corp.) which is prepared by the addition of 48.7 mCi $^{99m}$Tc-pertechnetate in 0.5 ml physiological saline obtained from the oxidant-free eluate of an $^{99}$Mo/$^{99m}$Tc radionuclide generator. The resulting exchange mixture was shaken and incubated for 30 minutes. The exchange labeled Zn, 99mTc-metallothionein was purified by size exclusion HPLC as in Example I. Following purification, 88% of the technetium-99m activity added to the Zn-metallothionein remained with the Zn, $^{99m}$Tc-MT. Assuming the technetium-99m is carrier-free, 16 pmoles of technetium-99m was exchanged into 0.5 mg of Zn-metallothionein.

EXAMPLE III

Preparation of Zn/$^{110m}$Ag-Metallothionein by Exchange Labeling of Zn-Metallothionein Zn-Metallothionein was prepared as described in Example II and dialyzed ["Spectra/Por 6" (2000 MWCO)] against 0.01M phosphate buffer (pH 7.0). $^{110m}AgNO_3$ in 0.5M $HNO_3$ obtained from New England Nuclear Corp. (specific activity = 1017 mCi/mmol) was neutralized to pH 7.0 by the additional of 0.5N $NH_4OH$. To 0.5 mg of Zn-metallothionein (0.5 ml; $10^{-4}$M) was add 50 uCi of $^{110m}Ag(NH_3)_2{}^+$. After a 30 minute incubation, the exchange labeled Zn/$^{110m}$Ag-MT was purified by size exclusion HPLC as in Example I. Following purification, 70% of the silver-110 activity added as $^{110m}Ag(NH)_2{}^+$ remained with the Zn/$^{110m}$Ag-MT, i.e. 34 nmoles of silver-110m exchanged into 0.5 mg of Zn-MT. Because there is no isotope effect with regard to metallothionein preparation, the substitution of $^{111}Ag(NH_3)_2{}^+$ for $^{110m}Ag(NH_3)_2{}^+$ will give comparable results.

EXAMPLE IV

Preparation and Evaluation of Zn, $^{99m}$Tc-Metallothionein (MT)/anti THY 1.1 Conjugate a. Preparation of Zn, $^{99m}$Tc-MT/anti THY 1.1 Conjugate To Zn-metallothionein (1.0 mg/ml; $10^{-4}$M) in 0.01M phosphate buffer (pH 7.0) was added glutaraldehyde (1 mg; final concentration of $10^{-2}$M). After one hour at room temperature, the unreacted glutaraldehyde was removed by dialysis ["Spectra/Por 6" (2000 MWCO)] for six hours against 0.01M phosphate buffer (pH 7.0). To 0.5 ml of this glutaraldehyde-treated metallothionein ($10^{-4}$M) was added 1 mg in 0.5 ml of 0.2M bicarbonate buffer (pH 9.5) of the monoclonal antibody (MAb) anti-THY 1.1. Reaction between the anti-THY 1.1 and glutaraldehyde-treated Zn-metallothionein was continued at 4° C. at pH 9.3 for eighteen hours, when 0.1 ml of a solution of 0.5M Tris/0.1M $NaBH_4$ was added. After reduction for one hour at room temperature, the Zn-metallothionein/anti-THY 1.1 conjugate was dialyzed for twenty-four hours ["Spectra/Por 6" (50,000 MWCO)] against 0.01M phosphate buffer (pH 6.8) to remove move unreacted sodium borohydride and glutaraldehyde treated Zn-metallothionein. To 0.1 mg of this conjugate was added 3.5 mCi of $^{99m}$Tc-GLUCOSCAN ™ (New England Nuclear Corporation), and the mixture was incubated for thirty minutes. The exchange labeled Zn, $^{99m}$Tc-metallothionein/anti-THY 1.1 conjugate was purified by HPLC utilizing a BioRad TSK-250 gel filtration column (available from BioRad Corporation) eluting with 0.1M phosphate buffer (pH 7.0) at 1.0 ml/minute. Following purification, 0.53 mCi of $^{99m}$Tc remained with the Zn, $^{99m}$Tc-MT/anti-THY 1.1 conjugate (0.1 mg).

b. Binding of Zn, $^{99m}$Tc-MT/anti-THY 1.1 Conjugate to Murine SL1 and SL2 Tumor Cells.

The reactivity of the Zn, $^{99m}$Tc-MT/anti-THY 1.1 conjugate toward antigen was assessed using the cell binding assay described by L. L. Houston, R. C. Nowinski, and I. D. Bernstein [*J. Immunol.*, 125, 837(1980)] in which murine SL1 and SL2 tumor cells were substituted for AKR/Jackson and AKR/Cumberland thymocytes. The SL1 (THY 1.1 antigen negative) and SL2 (THY 1.1 antigen positive) tumor cells [R. C. Nowinski et al, *Virology*, 81, 363, (1977)] were grown at 37° C. in a humidified 6% $CO_2$ incubator in Roswell Park Memorial Institute (RPMI) 1640 medium supplemented with 20% horse serum and 20 mM L-glutamine. Growth rates of cells were approximately three-fold per day for SL1 and five-fold per day for SL2. Tumor cells for use in the assay were isolated, resuspended in RPMI 1640 medium, and counted using standard techniques. Both SL1 and SL2 cells were incubated with Zn, $^{99m}$Tc-MT/anti-THY 1.1 (28 nCi of conjugate; 5 mCi/mg) or Zn, $^{99m}$Tc-MT (482 nCi of MT; 395 mCi/mg) for thirty minutes, separated from unbound MAb by centrifugation, washed, and counted for $^{99m}$Tc activity. Approximately 55% of the $^{99m}$Tc-labeled anti-THY 1.1 was bound to the antigen positive SL2 cells while little or no $^{99m}$Tc-labeled conjugate was bound to the antigen negative SL1 cells. In fact, a plot of $^{99m}$Tc-labeled anti-THY 1.1 vs. concentration of antigen tested showed no signs of leveling off at 55% binding. There was little or no binding of unconjugated $^{99m}$Tc-labeled MT to either the SL1 or SL2 tumor cells. In conclusion, the binding of anti-THY 1.1 by antigen was largely unaffected by its conjugation MT, and the Zn, $^{99m}$Tc-MT/anti-THY 1.1 conjugate retains the specificity for antigen observed with anti-THY 1.1. Therefore, addition of the $^{99m}$Tc-MT has surprisingly little effect on the biologically specificity of the anti-THY 1.1.

EXAMPLE V

Preparation and Evaluation of Zn, $^{99m}$Tc-Metallothionein/Anti Human Breast Carcinoma B6.2 a. Preparation of Zn, $^{99m}$Tc-MT/B6.2 Conjugate

The production described in Example IV for the preparation of Zn, $^{99m}$Tc-metallothionein/anti-THY 1.1 was followed using 0.6 mg of Zn-MT ($5 \times 10^{-5}$M), 1 mg of glutaraldehyde, and 3 mg of anti-human breast carcinoma B6.2. After final dialysis of Zn-MT/B6.2 against 0.01M phosphate buffer containing 0.15M NaCl (pH 8.0) for six hours then against 0.01M phosphate buffer containing 0.15M NaCl (pH 7.0) for eighteen hours ["Spectra/Por 6" (50,000 MWCO)], the conjugate (2 mg) was exchange labeled by adding 150 mCi of $^{99m}$Tc-GLUCOSCAN ™ (New England Nuclear Corporation) and mixing for thirty minutes. The $^{99m}$Tc-MT-labeled B6.2 was purified by size exclusion HPCL using a BioRad TSK-250 gel filtration column eluting with 0.1M phosphate buffer (pH 7.0) at 1.0 ml/min. Following purification, 30 mCi of the $^{99m}$Tc remained with the Zn, $^{99m}$Tc-MT/B6.2 conjugate.

b. Binding of Zn, $^{99m}$Tc-MT/B6.2 to Human MCF-7 and A375 Tumor Cells

The effect that conjugation of MT has on the ability of the MAb B6.2 to bind the antigen against which it is targeted was assessed in a cell binding assay which utilized two human tumor cell lines maintained in tissue culture, i.e., a human breast carcinoma MCF-7 [H. D. Soule, J. Vazguerz, A. Long, S. Alberg, and M. Brennan, *J. Natl. Cancer Inst.*, 51: 1409–1416 (1973)] and a human melanoma A375 [D. J. Giard, S. A. Aaronson, G. J. Todaro, P. Arnstein, J. H. Kersy, H. Dosik, and W. P. Parks, *J. Natl. Cancer Inst.*, 51: 1417 (1973)]. The MCF-7 tumor cells possess the antigen to which B6.2 binds [D. Colcher, et al., *Proc. Natl. Acad. Sci. USA*, 78: 3199 (1981)] while the A375 cells do not; they serve as a control on nonspecific binding of radiolabeled B6.2. Tumor cells for use in the assay are obtained by the following procedure. Three to four days after seeding, a trypsin/EDTA reagent (Cat. #610-5300, Gibco Laboratories, Grand Island, N.Y.) was added to monolayers of tumor cells in the place of growth medium. After shaking for one to two minutes, the trypsin/EDTA mixture was removed and replaced by a fresh aliquot of the same mixture. The resulting mixture was incubated at 37° C. for five to ten minutes to ensure complete cell detachment. The cells were suspended in RPMI 1640 medium containing 1% bovine serum albumin (BSA), and were counted using standard techniques. The MCF-7 and A375 cells prepared in this way were incubated with Zn, $^{99m}$Tc-MT/B6.2 (0.01665 uCi of conjugate; 1.53 mCi/mg) at 37° C. for two hours in microcentrifuge tubes coated with BSA. At the end of incubation, the cells were separated from unbound MAb by centrifugation, washed three times with RPMI 1640 medium (+1% BSA) and counted for $^{99m}$Tc activity. About 70% of the Tc-labeled B6.2 bound to antigen positive MCF-7 cells in single cell suspension, while there was less than 5% of the $^{99m}$Tc activity associated with the control A375 cells. As observed with the anti-THY 1.1 MAb, conjugation of MT to B6.2 results in a complex whose specificity for the antigen was generally retained.

c. In Vivo Pharmacokenitics of Zn, $^{99m}$Tc-Metallothionein/B6.2

Radioiodinated B6.2 has been shown to target human breast carcinoma xenographs in athymic mice in vivo. (D. Colcher, M. Zalutsky, W. Kaplan, D. Kufe, F. Austin, J. Schlom, *Cancer Research*, 43: 736 (1983)]. To determine the influence which the conjugation of MT has on the ability of B6.2 to target human breast carcinoma, $^{99m}$Tc-labeled MT/B6.2 was evaluated in athymic mice bearing Clouser or A375 solid tumors. Clouser tumors [B. C. Giovanella, J. S. Stehlin, L. J. Williams, S. S. Lee, and R. C., Shepart, *Cancer*, 47: 2269 (1978)], B6.2 antigen positive, and A375 tumors [D. J. Giard, S. A. Aaronson, G. J. Todaro, P. Arnstein, J. H. Kersy, H. Dosik, and W. P. Parks, *J. Natl. Cancer Inst.*, 51: 1417 (1973)], B6.2 antigen negative, were grown at a subcutaneous site on the dorsal surface of athymic mice. Each mouse (17–25 g) bearing 200–600 mg tumor was injected with 50 uCi of Zn, $^{99m}$Tc-MT/B6.2 and sacrificed at various times (three to four mice per time point) over forty-eight hours. Selected organs were removed, weighed, and counted for $^{99m}$Tc activity. The percent injected dose per gram of Zn, $^{99m}$Tc-MT/B6.2 found in antigen positive (Ag+) Clouser and the nonspecific antigen negative (Ag−) control A375 tumor are given in Table III. Based on the data shown in Table III, the Zn, $^{99m}$Tc-MT/B6.2 retains the ability of B6.2 to target human breast carcinoma in vivo, particularly at twenty-four hours when the uptake in the Clouser tumor, relative to A375, is approximately three to one. When compared to published biodistribution data for radioiodinated B6.2 (Colcher, et al., op. cit. (1983)), the $^{99m}$Tc-labeled B6.2 clears from the blood much more rapidly. In conclusion, the conjugation of MT to B6.2 does not compromise its ability to localize specifically in human breast carcinoma but accelerates clearance of the radiolabeled B6.2 from the blood

TABLE III

| $^{99m}$Tc-Metallothionein/B6.2 (% injected dose/gram) | | | | | |
|---|---|---|---|---|---|
| TUMOR TYPE | ORGAN | TIME (HOURS) | | | |
| | | 1 | 6 | 24 | 48 |
| Clouser | Tumor | 3.37 ± 0.39 | 7.72 ± 3.38 | 17.00 ± 4.50 | 6.18 ± 1.01 |

TABLE III-continued

| | | $^{99m}$Tc-Metallothionein/B6.2 (% injected dose/gram) | | | |
|---|---|---|---|---|---|
| TUMOR | | TIME (HOURS) | | | |
| TYPE | ORGAN | 1 | 6 | 24 | 48 |
| | Blood | 33.62 ± 2.83 | 13.58 ± 2.29 | 7.74 ± 6.04 | 2.53 ± 0.24 |
| | Spleen | 13.99 ± 3.36 | 14.17 ± 3.06 | 34.66 ± 14.48 | 5.64 ± 0.49 |
| | Liver | 15.72 ± 1.78 | 14.53 ± 0.97 | 21.93 ± 4.74 | 3.61 ± 0.71 |
| | Kidney | 18.07 ± 0.91 | 14.27 ± 2.42 | 18.54 ± 2.34 | 3.50 ± 0.59 |
| | Muscle | 0.96 ± 0.14 | 0.86 ± 0.11 | 2.92 ± 2.00 | 0.52 ± 0.16 |
| | Lung | 10.25 ± 1.53 | 4.76 ± 0.68 | 2.11 ± 0.46 | 1.17 ± 0.14 |
| A375 | Tumor | 2.63 ± 1.30 | 1.98 ± 1.06 | 5.41 ± 0.47 | 2.15 ± 0.24 |
| | Blood | 31.05 ± 3.80 | 17.13 ± 1.06 | 6.49 ± 7.57 | 6.95 ± 0.08 |
| | Spleen | 17.43 ± 9.33 | 9.58 ± 4.05 | 23.53 ± 10.43 | 6.25 ± 4.30 |
| | Liver | 15.42 ± 6.08 | 12.94 ± 2.39 | 16.28 ± 5.87 | 5.70 ± 0.72 |
| | Kidney | 17.06 ± 2.44 | 13.54 ± 1.52 | 18.01 ± 2.01 | 5.95 ± 0.75 |
| | Muscle | 1.62 ± 0.92 | 1.03 ± 0.25 | 2.31 ± 2.02 | 0.47 ± 0.66 |
| | Lung | 7.24 ± 0.69 | 6.14 ± 0.32 | 3.89 ± 1.38 | 2.69 ± 0.12 | d. Tumor Detection Using Zn, $^{99m}$Tc-MT/B6.2.

To show that the $^{99m}$Tc-labeled B6.2 would be useful for the detection of breast carcinoma, 200 uCi of Zn, $^{99m}$Tc-MT/B6.2 was injected intravenously into Clouser or A375 tumor-bearing athymic mice. Each animal was imaged using a standard gamma camera with 5.0 mm pinhole collimator. As early as six hours post-injection there was evidence of visible, specific accumulation of Zn, $^{99m}$Tc-MT/B6.2 in the Clouser tumor (Ag+) with no uptake evident in the A375 tumors (Ag−). The only other organ to appear in the image was the liver. At twenty-four hours post-injection, the Clouser tumor was clearly delineated. The $^{99m}$Tc counts observed in the tumor appeared to equal those observed in the liver. There was also activity in the bladder and kidney. In contrast, there was no visible accumulation of the $^{99m}$Tc-labeled B6.2 in A375 tumors. These results demonstrate the rapid and specific localization of a $^{99m}$Tc-labeled MT/B6.2 in breast tumor tissue in vivo, and the utility which $^{99m}$Tc-labeled MAb can have in the diagnosis and staging of breast cancer in humans.

EXAMPLE VI

Preparation and Evaluation of Zn, $^{99m}$Tc-Metallothionein/Anti-Human Breast Carcinoma B6.2 F(ab')$_2$ a. Preparation of Zn, $^{99m}$Tc-MT/B6.2 F(ab')$_2$.

A solution of pepsin (60 ug) obtained from Sigma Chemical Company, St. Louis, Mo., and anti human breast carcinoma B6.2 (3 mg) in 3 ml of 0.1M sodium acetate buffer (pH 4.0) was incubated at 37° C. overnight. The proteolytic fragments generated were separated from B6.2 F(ab')$_2$ by dialysis at 4° C. [Spectra/Por 6 (50,000 MWCO)] against 0.05M sodium phosphate buffer (pH 7.0 containing 0.15M sodium chloride. The B6.2 F(ab')$_2$ was analyzed by size exclusion HPLC using a BioRad TSK-250 column eluting with 0.1M sodium phosphate buffer (pH 7.0) at 1.0 ml/minute and non-reducing SDS polyacrylamide gel electrophoresis Following a second dialysis to bring the B6.2 F(ab')$_2$ into 0.2M carbonate/bicarbonate buffer (pH 9.5), the conjugation with Zn-MT was accomplished as described for B6.2 in Example V using 0.6 mg of Zn-MT and 1 mg of glutaraldehyde. The Zn-MT/B6.2 F(ab')$_2$ (1.56 mg) was exchanged labeled by adding 165 mCi of $^{99m}$Tc-GLUCOSCAN TM (New England Nuclear Corporation) and mixing for thirty minutes. After purification on size exclusion HPLC using a BioRad TSK-250 gel filtration column by eluting with 0.1M phosphate buffer (pH 7.0) at 1.0 ml/minute, 17.6 mCi of $^{99m}$Tc remained with the Zn, $^{99m}$Tc-MT/B6.2 F(ab')$_2$.

b. Binding of Zn, $^{99m}$Tc-MT/B6.2 F(ab')$_2$ Conjugate.

The effect of conjugation of MT on the reactivity of the F(ab')$_2$ dimer of B6.2 toward the antigen against which B6.2 is targeted was assessed using the cell binding assay described in part b of Example V. The Zn, $^{99m}$Tc-MT/B6.2 F(ab')$_2$ conjugate (2.29 ng; specific activity=11.3 uCi/ug) was incubated with varying concentrations of MCF-7 (Ag+) and A375 (Ag−) cells, and the percent $^{99m}$Tc-labeled conjugate bound was determined. The results indicate that 70–80% of the $^{99m}$Tc-labeled conjugate was bound to target MCF-7 cells while less than 5% was bound to the non-target A375 cells. Thus, the conjugation of Zn-MT to the F(ab')$_2$ of B6.2 does not diminish its binding by the antigen nor does it alter its specificity for the antigen.

c. In Vivo Pharmacokinetics of Zn, $^{99m}$Tc-MT/B6.2 F(ab')$_2$.

The ability of radioiodinated B6.2 F(ab')$_2$ to target human breast carcinoma xenographs in athymic mice has been demonstrated by Colcher, et al. [Colcher, et al., op. cit. (1983)]. Using Clouser and A375 tumor-bearing athymic mice, the in vivo specificity and pharmacokinetics of Zn, $^{99m}$Tc-MT/B6.2 F(ab')$_2$ were determined. Each tumor-bearing mouse was injected with 48.5 uCi of $^{99m}$Tc-labeled F(ab')$_2$ conjugate (specific activity=6.7 uCi/ug), and the percent injected dose per gram at various time points was determined and are tabulated in Table IV. The ratio of Clouser vs. A375 tumor uptake at twenty-four hours is about two to one clearly demonstrating the retention of tumor specificity of the B6.2 F(ab')$_2$ following MT conjugation. The blood clearance of $^{99m}$Tc-labeled B6.2 F(ab')$_2$ was about the same as that observed with the $^{99m}$Tc-labeled intact B6.2. Thus, the specificity of $^{99m}$Tc-labeled B6.2 F(ab')$_2$ and its rapid blood clearance indicate that fragments of B6.2 labeled with MT have utility for in vivo targeting of tumor similar to that observed for Zn, $^{99m}$Tc-MT/intact B6.2.

TABLE IV

| | | $^{99m}$Tc-Metallothionein-B6.2-F(ab')$_2$ (% injected dose/gram) | | | |
|---|---|---|---|---|---|
| TUMOR | | TIME (HOURS) | | | |
| TYPE | ORGAN | 1 | 4 | 16 | 26 |
| Clouser | Tumor | 3.98 ± 0.56 | 6.45 ± 1.36 | 6.08 ± 0.68 | 4.54 ± 0.64 |
| | Blood | 32.54 ± 12.95 | 27.71 ± 3.05 | 11.47 ± 1.27 | 7.35 ± 1.36 |
| | Spleen | 5.71 ± 0.53 | 6.00 ± 0.58 | 6.20 ± 0.99 | 4.81 ± 0.39 |
| | Liver | 38.20 ± 5.01* | 45.60 ± 13.46 | 36.09 ± 10.06 | 53.72** |
| | Kidney | 7.45 ± 1.00* | 6.78 ± 1.59 | 5.89 ± 2.46 | 2.28** |
| | Muscle | 2.91 ± 2.50 | 1.84 ± 0.20 | 1.39 ± 0.47 | 2.18 ± 1.37 |
| | Heart | 10.66 ± 3.64 | 10.38 ± 2.26 | 4.76 ± 0.76 | 2.99 ± 0.88 |

TABLE IV-continued $^{99m}$Tc-Metallothionein-B6.2-F(ab')$_2$ (% injected dose/gram)

| TUMOR TYPE | ORGAN | TIME (HOURS) | | | |
|---|---|---|---|---|---|
| | | 1 | 4 | 16 | 26 |
| | n = | 3 | 3 | 3 | 3 |
| A375 | Tumor | 2.56 ± 1.30 | 3.46 ± 1.73 | 2.97 ± 0.54 | 2.07** |
| | Blood | 30.70 ± 5.41 | 27.63 ± 1.73 | 10.95 ± 0.64 | 5.72 |
| | Spleen | 7.23 ± 0.77 | 7.22 ± 0.49 | 6.28 ± 0.79 | 4.01 |
| | Liver | 51.53 ± 10.77 | 46.96 ± 18.98 | 33.45 ± 13.10* | 9.06 |
| | Kidney | 6.60 ± 1.08 | 8.60 ± 3.23 | 6.55 ± 0.32* | 10.24 |
| | Muscle | 1.76 ± 0.49 | 2.00 ± 0.82 | 2.29 ± 1.88 | 0.90 |
| | Heart | 8.01 ± 1.38 | 9.37 ± 2.27 | 3.19 ± 1.66 | 4.33 |
| | n = | 3 | 3 | 3 | 1 |

*n = 2
**n = 1

I claim:

1. A conjugate of (a) a target-seeking biologically active molecule selected from the group consisting of antibodies, antibody fragments, hormones, peptides, proteins and drugs which bind to receptors and localize in certain organs, tissues and cells of the mammalian body and (b) metallothionein or metallothionein fragment in which at least a part of the metal in the metallothionein or fragment is a trace-labeled metal having sufficient affinity for the metallothionein or metallothionein fragment to bind thereto.

2. The conjugate of claim 1 wherein the trace-label metal is selected from the group consisting of Pb, Tc, Ru, Hg, Ag, Au, Pd, Cu, Re, Bi, Pt, W, Co, Ni, Rh and Os.

3. The conjugate of claim 1 wherein the trace-label metal is a radionuclide.

4. The conjugate of claim 3 wherein the radionuclide is selected from the group consisting of Tc-99m, Pb-203, Ru-97, Hg-197, Ag-111, Au-198, Pd-103, Cu-67, Re-188, Bi-212, Os-191.

5. The conjugate of claim 3 wherein the radionuclide is selected from the group consisting of Tc-99m, Hg-197, Ag-111, Au-198, Pd-103, Cu-67, Re-188, and Ru-97.

6. The conjugate of claim 3 wherein the radionuclide is selected from the group consisting of Tc-99m, Hg-197, Ag-111, and Au-198.

7. The conjugate of claim 4, 5 or 6 in which the target-seeking biologically active molecule is an antibody or fragment thereof.

8. The conjugate of claim 7 wherein the antibody is a monoclonal antibody.

9. The conjugate of claim 8 wherein the monoclonal antibody is selected from the group consisting of anti-THY 1.1 and anti human breast carcinoma B6.2.

10. The conjugate of claim 9 wherein the metallothionein or metallothionein fragment is mammalian.

11. The conjugate of claim 7 wherein the metallothionein or metallothionein fragment is mammalian.

12. A conjugate of (a) a target-seeking biologically active molecule selected from the group consisting of antibodies, antibody fragments, hormones, peptides, proteins and drugs which bind to receptors and localize in certain organs, tissues and cells of the mammalian body and (b) metallothionein or metallothionein fragment in which all metal in the metallothionein or fragment
 (a) is non-radioactive and
 (b) has an affinity for metallothionein less than that of the cations selected from the group consisting of Tc, Ag, Au, Hg and Cu.

13. The conjugate of claim 12 wherein the non-radioactive metal is Zn.

14. The conjugate of claim 12 or 13 in which the target seeking biologically active molecule is an antibody or fragment thereof.

15. The conjugate of claim 14 wherein the antibody is a monoclonal antibody.

16. The conjugate of claim 15 herein the monoclonal antibody is selected from the group consisting of anti-THY 1.1 and anti-human breast carcinoma B6.2.

17. The conjugate of claim 16 wherein the metallothionein or metallothionein fragment is mammalian.

18. The conjugate of claim 14 wherein the metallothionein or metallothionein fragment is mammalian.

19. A composition comprising purified metallothionein or metallothionein fragment in which at least a part of the metallothionein or fragment is Tc-99m, in a physiologically compatible vehicle in an amount sufficient for scintigraphic imaging.

20. The composition of claim 19 wherein the metallothionein or metallothionein fragment is mammalian.

21. In a method of diagnosing a disease state or monitoring organ function in a mammal which comprises administering a trace labeled conjugate of a target-seeking biologically active molecule, then subjecting the mammal to scintigraphic imaging, the improvement wherein the conjugate is a conjugate of claim 1, 2, 3, 4, 5 or 6 in a physiologically compatible vehicle in an amount effective for scintigraphic imaging.

22. A method of treating a disease state in a mammal which comprises administering a conjugate of claim 5 wherein the trace-label metal is a radionuclide and is selected from the group consisting of Ag-111, Au-198, Sb-119, Cu-67, Re-188 and Pd-103 and wherein said radionuclide is in a physiologically compatible vehicle in an amount sufficient to kill target cells.

23. A method of monitoring kidney function comprising intravenously administering to a mammal a composition of claim 19 or 20, then subjecting the mammal to scintigraphic imaging wherein the imaging is an indication of kidney function.

24. A method of trace labeling a target-seeking biologically active molecule which comprises
 (a) reacting a metallothionein or fragment thereof with a salt or salt complex of a trace-label metal having a sufficient affinity for the metallothionein or fragment to bind thereto whereby the trace-label metal replaces at least a portion of the metal in the metallothionein, and then
 (b) conjugating the metallothionein to the biologically active molecule selected from the group consisting of antibodies, antibody fragments, hormones, peptides, proteins and drugs which bind to receptors and localize in certain organs, tissues and cells of the mammalian body.

25. The method of claim 24 wherein the trace-label metal is a radionuclide.

26. The method of claim 24 or 25 wherein the biologically active molecule is an antibody or fragment thereof.

27. The method of claim 26 wherein the antibody is a monoclonal antibody.

28. The method of claim 27 wherein the monoclonal antibody is selected from the group consisting of anti-THY 1.1 and anti-human breast carcinoma B6.2.

29. The method of claim 25 wherein the radionuclide is selected from the group consisting of Tc-99m, Ag-111, Au-198 and Hg-197.

30. A method of trace labeling a biologically active molecule body which comprises
   (a) reacting a thionein with a salt or salt complex in which at least a portion of the metal is a trace-label metal, whereby thionein is converted to a metallothionein containing at least a portion of trace-label metal, and then
   (b) conjugating the metallothionein to the biologically active molecule selected from the group consisting of antibodies, antibody fragments, hormones, peptides, proteins and drugs which bind to receptors and localize in certain organs, tissues and cells of the mammalian body.

31. The method of claim 30 wherein the biologically active molecule is an antibody or fragment thereof.

32. The method of claim 31 wherein the antibody is a monoclonal antibody.

33. The method of claim 32 wherein the monoclonal antibody is selected from the group consisting of anti-THY 1.1 and anti-human breast carcinoma B6.2.

34. The method of claim 30, 31, 32 or 33 wherein the trace-label metal is a radionuclide.

35. The method of claim 34 wherein the radionuclide is selected from the group consisting of Ru-97, Pd-103 and.

36. A method of trace-labeling a biologically active molecule which comprises
   (a) conjugating metallothionein, thionein, or a fragment thereof with a biolgically active molecule selected from the group consisting of antibodies, antibody fragments, hormones, peptides, proteins and drugs which bind to receptors and localize in certain organs, tissues and cells of the mammalian body and then
   (b) reacting a conjugate formed from step (a) with a salt or salt complex of a trace-label metal having a sufficient affinity for the metallothionein, thionein or fragment thereof to bind thereto, whereby the trace-label metal replaces at least a portion of the metal in the metallothionein or the thionein is converted to a metallothionein containing at least a portion of trace-label metal.

37. The method of claim 36 wherein the biologically active molecule is an antibody or fragment thereof.

38. The method of claim 37 wherein the trace-metal is a radionuclide.

39. In a method of diagnosing a disease state or monitoring organ function in a mammal which comprises administering a trace-labeled conjugate of a target-seeking biologically active molecule, then subjecting the mammal to scintigraphic imaging, the improvement wherein the conjugate is a conjugate of claim 7 in a physiologically compatible vehicle in an amount effective for scintigraphic imaging wherein the imaging is an indication of a disease state or of organ function.

40. In a method of diagnosing a disease state or monitoring organ function in a mammal which comprises administering a trace-labeled conjugate of a target-seeking biologically active molecule, then subjecting the mammal to scintigraphic imaging, the improvement wherein the conjugate is a conjugate of claim 8 in a physiologically compatible vehicle in an amount effective for scintigraphic imaging wherein the imaging is an indication of a disease state or of organ function.

41. In a method of diagnosing a disease state or monitoring organ function in a mammal which comprises administering a trace-labeled conjugate of a target-seeking biologically active molecule, then subjecting the mammal to scintigraphic imaging, the improvement wherein the conjugate is a conjugate of claim 9 in a physiologically compatible vehicle in an amount effective for scintigraphic imaging wherein the imaging is an indication of a disease state or of organ function.

42. A method of claim 22 wherein the target-seeking biologically active molecule is an antibody or fragment thereof.

43. A method of claim 42 wherein the antibody is a monoclonal antibody.

44. A method of claim 43 wherein the monoclonal antibody is selected from the group consisting of anti-THY 1.1 and antihuman breast carcinoma B6.2.

* * * * *